United States Patent [19]

McDonald et al.

[11] Patent Number: 4,479,859
[45] Date of Patent: Oct. 30, 1984

[54] LASER PHOTOCHEMICAL SYNTHESIS OF BENZENE AND ITS DERIVATIVES

[75] Inventors: Joseph K. McDonald, Athens, Ala.; James A. Merritt, Pulaski, Tenn.

[73] Assignee: The United States of America as represented by the Secretary of the Army, Washington, D.C.

[21] Appl. No.: 565,807

[22] Filed: Dec. 27, 1983

[51] Int. Cl.³ .............................................. B01J 19/12
[52] U.S. Cl. .......................... 204/158 R; 204/162 R; 204/163 R
[58] Field of Search ............ 204/158 R, 162 R, 163 R, 204/158 L

[56] References Cited
PUBLICATIONS

J. I. Steinfeld, Editor, *Laser-Induced Chemical Processes*, Plasma Press, New York, 1981, pp. 86–87 and Chapter 4, pp. 243–267.

*Primary Examiner*—Howard S. Williams
*Attorney, Agent, or Firm*—Anthony T. Lane; Robert P. Gibson; Jack W. Voigt

[57] ABSTRACT

A cw $CO_2$ tunable laser is employed to irradiate an allyl halide selected from allyl chloride, allyl bromide, allyl fluoride, 2-methyl-3-chloropropene, and 2,3-dichloropropene and contained in one or more reaction cells at a predetermined pressure. A predetermined power level from about 25 to 150 watts, an irradiating time from about 0.2 second to about 60 seconds, and a selected radiation line for example P(36), P(32), P(28), P(26), or P(22) (that is resonant with an absorption band of the selected allyl halide) are employed to achieve dissociation of the selected allyl halide and to achieve a laser-induced photochemical synthesis of benzene and substituted benzenes.

7 Claims, 8 Drawing Figures

LASER PHOTOCHEMICAL SYNTHESIS OF BENZENE AND ITS DERIVATIVES

DEDICATORY CLAUSE

The invention described herein may be manufactured, used, and licensed by or for the Government for governmental purposes without the payment to us of any royalties thereon.

BACKGROUND OF THE INVENTION

The recent widespread availability of tunable lasers has enhanced the interest in photochemical processes. The output of a carbon dioxide ($CO_2$) infrared laser is resonant with the vibrational frequencies of a wide range of organic molecules, and because of this resonance, this type of gas laser has become the most popular for studies of infrared laser-induced chemical processes. The absorption of the laser radiation by the molecules promotes the molecules into excited vibrational states, and the molecules can become very reactive as a result.

In principle, the energy of the laser can be deposited into a single vibrational mode and the vibration can be excited to the point of dissociation. The resulting reactive species would be expected to react further. However, energy relaxation within a given vibrational mode generally occurs on a time scale of picoseconds. For complex molecules there is also a redistribution of energy among different vibrational modes and rotational and translational levels. Furthermore, at pressures of a few torr and higher, intermolecular redistribution accompanies collisions. Consequently it has been concluded that only a few microseconds are required for a molecule (which has been excited by an infrared laser) to reach a thermal equilibrium. Once the energy of the laser has been distributed throughout the molecule, any reaction which proceeds would very likely be similar to an ordinary pyrolysis reaction. Even if the reactions are governed by thermal processes, the laser-induced reactions will generally differ from ordinary pyrolytic thermal reactions because wall reactions are essentially eliminated from the former. In that case, it should be possible to compare the results of laser-induced "thermal" reactions with those carried out in shock tubes.

As noted hereinabove laser energy has been deposited to achieve a level of excitation to the point of dissociation of molecules to give reactive species. In experiments the laser energy has been distributed throughout the molecules to proceed along a reaction mode which is somewhat similar to an ordinary pyrolysis reaction. The tunable $CO_2$ lasers have also been employed in elimination reactions. In fact, elimination reactions have been extensively investigated in polyatomic molecules exposed to an intense infrared laser field. The results obtained with organic halides have been the elimination of hydrogen halide and the formation of an alkene or alkyne compound. Some fragmentation of the parent molecule is also observed depending on the molecular size and laser fluence. However, recombination of radicals or thermally excited parent molecules to form larger molecules is usually not observed.

Pyrolysis of organic halides is found to follow several reaction paths, including unimolecular, radical chain, and bimolecular reactions. These reactions can produce simple and complex molecules by decomposition and radical addition.

As evidenced by the experimental activities relating to the use of tunable $CO_2$ lasers, a technology tool is now available which can lead to discoveries formerly associated only with thermal chemistry which produced many products in addition to the product desired thereby increasing costs associated with separation and purification of the desired product.

An object of this invention is to provide a laser photochemical synthesis method for the production of benzene and substituted benzenes.

A further object of this invention is to provide a laser photochemical synthesis method for the production of benzene and substituted benzenes wherein the yield of benzene and substituted benzenes are pressure—and laser power—dependent.

Still a further object of this invention is to provide a laser photochemical synthesis method wherein the final product produced is controlled by the allyl halide selected for laser-induced reaction and the predetermined pressure and laser power for the laser-induced reaction for production of benzene or substituted benzenes.

SUMMARY OF THE INVENTION

Cw $CO_2$ laser radiation is passed through ZnSe windows of a stainless steel reaction cell containing a reactant gas at a predetermined pressure range for producing a laser induced chemical reaction. The reactant gas is selected from allyl halides which produce benzene or substituted benzenes.

The dissociation of the reactant gas allyl chloride (3-chloropropene) induced by $CO_2$ laser irradiation produces some of the normal products expected (allene, propyne, acetylene, ethylene, and methane). However, benzene constitutes one of the major products in this dissociation reaction. When the reactant gases are 1,3-dichloropropene and 2-methyl, 3-chloropropene, benzene is produced but in lower yield than from the irradiation of the reactant gas allyl chloride (3-chloropropene). 2-3 dichloropropene also produces the chlorine-substituted benzene. The amount of benzene or substituted benzene formed is found to be pressure- and laser power-dependent, but the yield is determined to reach a plateau for each product produced at an optimized pressure and laser power for the laser induced chemical reaction.

$CO_2$ laser lines that overlap the vibrational absorption in the 900–1000 $cm^{-1}$ region induce a chemical reaction for producing benzene and substituted benzenes from selected reactant allyl halides.

DESCRIPTION OF THE PREFERRED EMBODIMENT

Figure 6:
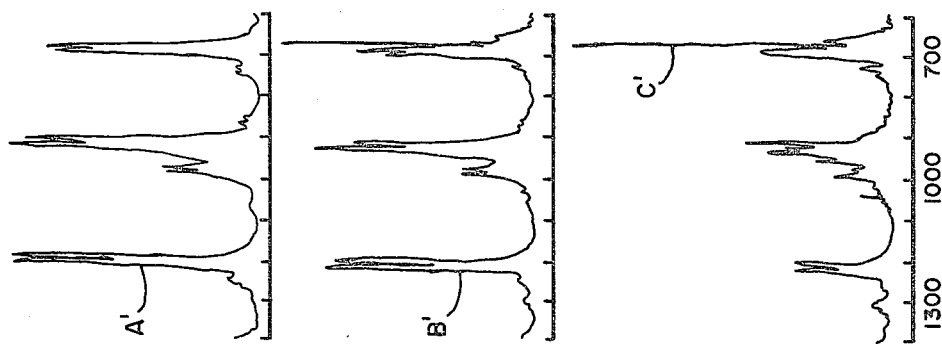
FIG. 6 is an infrared spectra of allyl bromide and the products produced from laser induced chemical reactions.

Allyl halides laser induced chemical reactions are initiated by an infrared laser beam transmitted through ZnSe windows secured at each end of a stainless steel cell (e.g., 5×10 cm.) equipped with O-ring seals for securing the windows (5 cm diameter) onto the cells. The infrared beam enters through ZnSe windows at either end of the cell (traversing a 10 cm path), and the infrared spectra of the cell contents were measured through KCl or ZnSe windows mounted perpendicular to the ZnSe windows (5 cm path).

The allyl halides exhibit a series of very strong absorption bands in the 900–1000 cm$^{-1}$ region which are resonant with the output of the $CO_2$ laser. This affords an opportunity for comparison of products produced from laser-induced reactions to pyrolysis experiments.

EXPERIMENTS

The samples allyl chloride, 2-methyl-3-chloropropene, and 2,3 dichloropropene are obtained commercially. Their stated purities range between 95 and 99% and each is used without further purification. Samples of allyl bromide and allyl fluoride were obtained from the Chemistry Department of the University of South Carolina. All sample transfers are performed using standard vacuum techniques.

The reactions are carried out in stainless steel cells (5×10 cm) equipped with O-ring seals for securing the windows (5 cm diameter) onto the cells as described hereinabove.

Infrared laser excitation in the range of 10.4 or 9.4 μm is provided by a Coherent Radiation Laboratories model 41 continuous-wave (cw) $CO_2$ laser. The exact laser frequencies are verified using an Optical Engineering $CO_2$ Spectrum Analyzer. In single-line operation, output powers up to 150 W can be obtained by varying the current and the ($CO_2$-$N_2$-He) gas mixture in the laser tube.

Infrared spectra are collected on a Digilab FTS-20 interferometer equipped with a KBr/Ge beamsplitter and a triglycine sulfate (TGS) detector. Interferograms are transformed after applying a trapezoidal apodization function with an effective spectral resolution of 1.0 cm$^{-1}$. This resolution is sufficient to allow unequivocal identification of products (and starting materials) to be made from the infrared frequencies.

EXPERIMENTAL RESULTS: ALLYL CHLORIDES AND BROMIDES

Allyl chloride exhibits infrared absorptions between 1010 and 880 cm$^{-1}$, and the most intense bands are between 940 and 920 cm$^{-1}$. The P(26) [00°1–10°0] line of the $CO_2$ laser at 938.69 cm$^{-1}$ is resonant with the wing of the bands assigned to the C—C stretch and the $CH_2$ wag, and this excitation frequency is used for most of the studies of allyl chloride.

Sample pressures are varied between 10 and 100 torr and laser powers are varied between 25 and 150 W. Irradiation times from 0.2 to 60 seconds are used. At low pressures (10 torr) and relatively low powers (50 W), no reaction of the allyl chloride is observed. At higher pressures (50–100 torr) a reaction is initiated using the range of laser powers given above. A luminescence is also observed during irradiation. The luminescence lasted approximately 3–4 seconds and the intensity is pressure-dependent.

Figure 1:
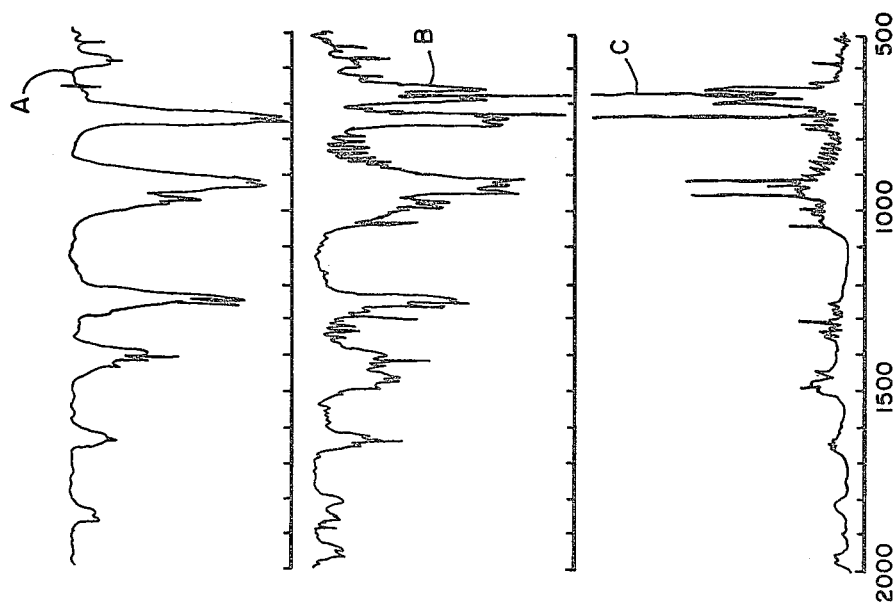
FIG. 1 depicts an infrared spectra of allyl chloride and the products produced from laser induced chemical reactions.

Further reference to the drawing indicates a spectra of FIG. 1 which is representative of typical results for the laser-induced reaction of allyl chloride. Curve A is an infrared spectra of allyl chloride while curve B is an infrared spectra of the mixture of allyl chloride and products. The absorbance spectrum of the products is curve C shown at the bottom of the figure and indicates the existence of propene, propyne, 1,3 cyclohexadiene (trace), benzene, acetylene, allene, ethene, methane, and butadiene. There are also large amounts of hydrogen chloride. The vibrational frequencies used to identify these compounds are summarized in Table I. These products differ from the reported pyrolysis products only in the absence of diallyl and butene.

Figure 2:
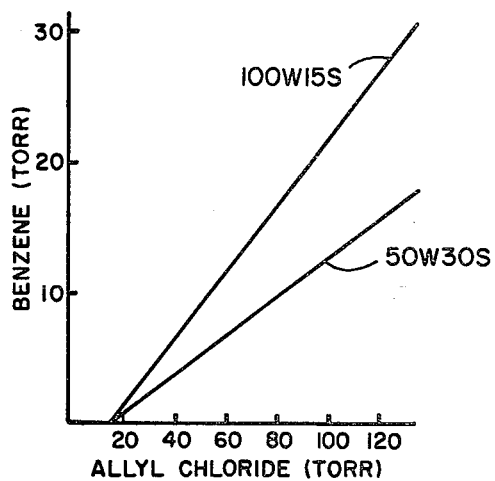
FIGS. 2–5 depict benzene yields as a function of allyl chloride with a 1500J laser irradiation energy at selected watts/$cm^2$, with a 1500J laser irradiation energy at selected allyl chloride pressures, with a 100 watt/$cm^2$ laser power at selected allyl chloride pressures, and product yields as a function of irradiation time, respectively.
Figure 3:
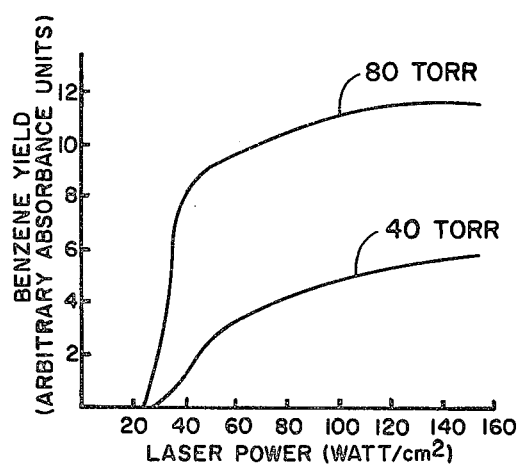
Figure 4:
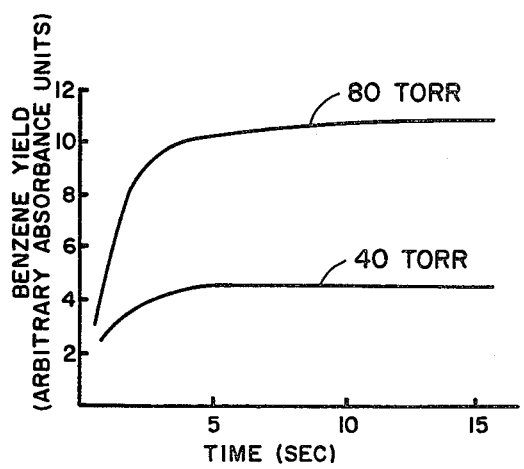

FIG. 2 is a plot of allyl chloride pressures versus benzene absorbances at 50 and 100 W for 30 and 15 seconds, curves 50 W350 and 100 W155, respectively. A laser fluence of 1500J units is chosen. The plot indicates that a threshold pressure of allyl chloride is needed for benzene production. The percent yield of benzene is determined to reach a steady state above 60 torr. A laser power dependence is also indicated from this figure and this is shown to be correct in FIG. 3 which depicts benzene yield from irradiation of 80 torr allyl chloride and 40 torr allyl chloride. It is observed that a threshold of laser power is required for a reaction to occur. The yield of benzene increases rapidly with laser power and then levels off. When laser irradiation time is varied at constant laser power and allyl chloride pressure (80 torr and 40 torr, respectively, as shown in FIG. 4), an optimum laser energy is indicated.

The pyrolysis of allyl chloride is reported to be a combination of radical non-chain and chain heterogeneous first-order reactions.

The main reactions in the proposed mechanism for the gas phase pyrolysis of allyl chloride are:

$$CH_2=CH-CH_2Cl \rightarrow CH_2=CH-CH_2\cdot + Cl \quad (1)$$

$$CH_2=CH-CH_2\cdot + CH_2=CH-CH_2Cl \rightarrow CH_2=CH-CH_3 + CH_2=CH-\overset{\cdot}{C}HCl \quad (2)$$

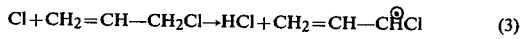

$$Cl + CH_2=CH-CH_2Cl \rightarrow HCl + CH_2=CH-\overset{\cdot}{C}HCl \quad (3)$$

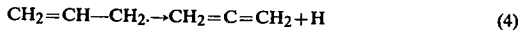

$$CH_2=CH-CH_2\cdot \rightarrow CH_2=C=CH_2 + H \quad (4)$$

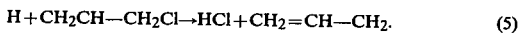

$$H + CH_2CH-CH_2Cl \rightarrow HCl + CH_2=CH-CH_2\cdot \quad (5)$$

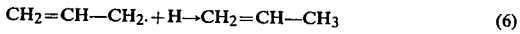

$$CH_2=CH-CH_2\cdot + H \rightarrow CH_2=CH-CH_3 \quad (6)$$

$$2CH_2=CH-CH_2\cdot \rightarrow C_6H_{10} \quad (7)$$

$$CH_2=CH-CH_2\cdot + CH_2=CH-\overset{\cdot}{C}HCl \rightarrow C_6H_8 + HCl \quad (8)$$

$$2CH_2=CH-CHCl \rightarrow C_6H_6 + 2HCl \quad (9)$$

At first it was believed that this mechanism could explain most of the products observed in the LIR experiments. However, when the ethene concentration was determined, it was found to be greater than propene. This mechanism only considers ethene to be a minor side product. New reactions must therefore be added to explain ethene as a main reaction product.

In the decomposition of a molecule there can be several reaction paths. Normally the preferred path is the one with the lowest activation energy. If the energy requirements for two reactions differ by a small amount, a higher temperature may allow the higher energy reaction to become competitive. This is believed to happen in the case of allyl chloride. Energy to break the C—C bond is not much greater than the energy of the C—C bond. In the initial laser irradiation a large temperature gradient is established in a small volume along the laser path. The temperature in this volume could easily exceed 1000 C. At these higher temperatures, the C—C bond, as well as the C—Cl bond can easily be broken.

Two initial steps are then possible. Reaction (1) and the reaction $$CH_2=CH—CH_2Cl \rightarrow CH_2=CH. + .CH_2Cl. \tag{10}$$

The ethene radical can react further with allyl chloride by the reaction $$CH_2=CH. + CH_2=CH—CH_2Cl \rightarrow C\text{-}H_2—CH_2 + CH_2=CH—.CHCl. \tag{11}$$

This reaction can explain the large yield of ethene observed. The ethene radical could also give up a hydrogen atom $$CH_2=CH. \rightarrow HC=CH + H. \tag{12}$$

Considering only Reactions (1), (2), (3) and (9), the stoichiometry is represented by $$3C_3H_5Cl \rightarrow C_3H_6 + C_6H_6 + HCl.$$

A one-to-one ratio of propene to benzene should be produced. If the yield of propene is subtracted from the yield of benzene, the ratio of ethene to remaining benzene is approximately 1.6:1. Reaction (11) produces one ethene molecule and one-half of the radical responsible for benzene. The postulated mechanism for the chloromethyl radical should not indicate the chloroallyl radical as a major project. With this restriction in mind, the following mechanism is postulated:

$$CH_2Cl. + CH_2=CH—CH_2Cl \rightarrow CH_2=CH—CH\text{-}Cl—CH_2. + HCl \tag{13}$$

$$CH_2=CH—CHCl—CH_2. \rightarrow CH_2=-CH=CH_2 + Cl \tag{14}$$

$$CH_2Cl. + CH_2=CH—CH_2. \rightarrow CH_2=-CH—CH=CH_2 + HCl \tag{15}$$

$$2CH_2Cl. \rightarrow CH_2Cl—CH_2Cl \tag{16}$$

$$CH_2Cl—CH_2Cl \rightarrow CH_2=CHCl + HCl \tag{17}$$

$$CH_2—CHCl \rightarrow CH \equiv CH + HCl \tag{18}$$

$$2C_2H_3. \rightleftharpoons C_4H_6. \tag{19}$$

Chloroethane or chloroethene are not observed as products, so if Reaction (16) occurs, Reaction (18) would have to be the end result. The high temperature of the decomposition makes this possible. The reverse of Reaction (19) could also explain the small amount of butadiene observed.

The mechanism explains the appearance of most of the observed products. Propyne (methyl acetylene) is the result of thermal isomerization of allene. This is shown to be true by laser-irradiating a sample of allene. Propyne is observed as a product in good yield.

The vibrational frequency of propene and diallyl overlaps at the strongest absorbance of diallyl. It is possible that trace quantities of diallyl are present. Instead of Reaction (7) forming diallyl, a disproportionation could also occur $$2CH_2=CH—CH_2. \rightarrow CH_2=C=CH_2 + CH_2=-CH—CH_3. \tag{7a}$$

The allyl radicals should be highly energetic and Reaction (7) would probably require a third body to occur while Reaction (7a) would not.

Methane is probably the result of some product decomposition into a methyl radical with subsequent hydrogen abstraction.

Figure 5:
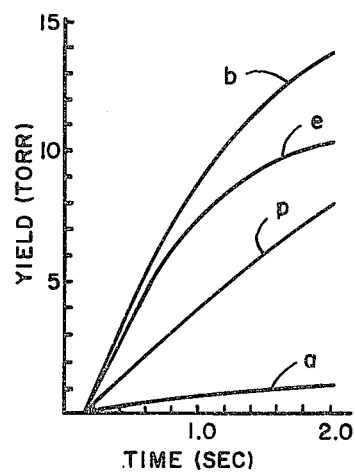

The LIR of allyl chloride is a reasonably slow reaction; therefore, a series of kinetic experiments are performed. A graphite shutter adjustable to 0.1 sec was used to control laser irradiation time. Samples of allyl chloride are irradiated from 0.1 to 1.9 sec at 75 and 100 W of laser power. The concentrations of allyl chloride, benzene, allene, hydrochloric acid, ethylene and propene are determined from their infrared spectra. A plot of the concentration of ethene (curve e), propene (curve p), benzene (curve b) and allene (curve a) versus irradiation time is shown in FIG. 5 for one of the kinetic runs. A steady rise in concentration of ethene, propene, and benzene is observed while a leveling-off of allene is noted. The concentrations of methane and acetylene also continued to increase with irradiation time.

Various functional plots of allyl chloride concentrations versus time indicated that the best straight line plot is obtained for a three-halves reaction order. For confirmation of this result, initial rates at two different concentrations were obtained.

Since various pressures of allyl chloride absorb different amounts of laser fluence, the effective temperature of the reaction would be different and therefore the rate constant. To overcome this problem, laser lines were chosen so that the amount of absorbance would be approximately equal. The P(8), 954.55 cm$^{-1}$, and P(26), 938.69 cm$^{-1}$ CO$_2$ laser lines are used for 80 and 40 torr of allyl chloride, respecrively. The results of these kinetic experiments are given in Table II. The ratio of the initial rates again indicated a three-halves reaction order.

This result confirmed that the LIR of allyl chloride follows a three-halves reaction order. This order disagreed with the first-order rate reported in the pyrolysis experiments. The three-halves order could be the result of a low pressure, high temperature mechanism or represent overall order of competing mechanisms. A 3/2 order is not unexpected since the overall order in the pyrolysis of propene is 3/2 order.

Allyl Bromide (3-bromopropene)

The infrared absorption of allyl bromide has the same fundamental vibrations in the 900–1000 cm$^{-1}$ region as allyl chloride with only slight shifts in the absorbance maximum. LIR of allyl bromide should be similar to that observed for allyl chloride.

The P(36), 929.02 cm$^{-1}$ line of the CO$_2$ laser is used for most of the investigations. As expected, laser irradiation of allyl bromide produces essentially the same compounds as allyl chloride (compare FIG. 1 curves A, B and C with FIG. 6, curves A$^1$, B$^1$, and C$^1$ representing the infrared spectra of allyl bromide, the infrared spectra of mixture of allyl bromide and product, and the infrared spectra of the products, respectively). Hydrogen bromide, benzene, propene, ethylene, acetylene and methane are the most abundant products (see Table I). Only trace quantities of allene and propyne and no detectable cyclohexadiene are observed. A pressure-dependent weak glow is observed along the laser path during irradiation and a carbon deposit is also observed on the cell walls and windows.

Figure 7:
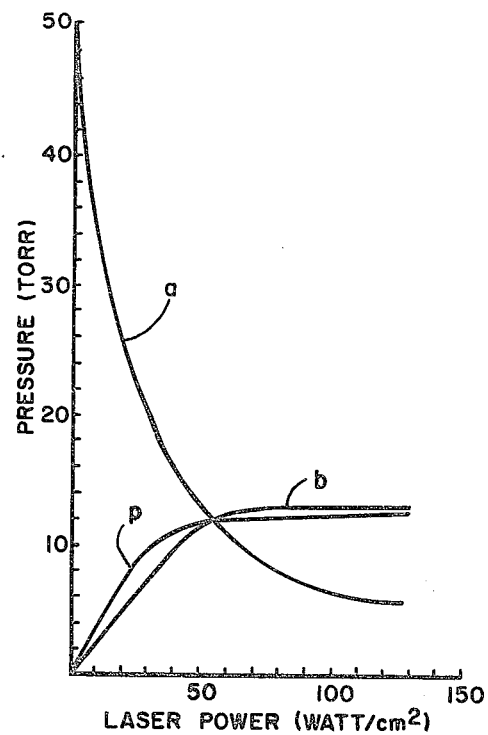
FIG. 7 depicts the dependence of decomposition of allyl bromide to laser power at a constant 1000J laser irradiation energy.

A reactant (allyl bromide, curve a) and product (propene, curve p and benzene, curve b) concentration as a function of laser power was determined at an arbitrary 1000 J laser fluence (See curves of FIG. 7). A laser power threshold is not indicated for the bromide. Above 100 W, the reaction appears to be independent of laser power. However, the optimum laser power for the percent yield of benzene and propene production is 50–80 W. Higher powers tend to produce more of the side products and solid deposits. The approximate 31% Yield of benzene for allyl bromide consumed compares very favorably to a theoretical 33% yield.

A reaction order for allyl bromide is also determined using 25 and 50 torr. P(36), 929.02 cm$^{-1}$, and P(22), 942.38 cm$^{-1}$ CO$_2$ laser lines are utilized on the 25 and 50 torr, respectively. The ratio of the initial rates indicates that allyl bromide follows an overall first order reaction. This order agrees with the results obtained from pyrolysis experiments. It is noted in the 25 torr kinetic run as the concentration decreased the overall reaction order tends to be second order. The allyl bromide concentration becomes sufficiently low that a bimolecular initiation reaction is required.

The overall mechanism is essentially the same as obtained in pyrolysis and may be represented by:

$$CH_2=CH-CH_2Br \rightarrow CH_2=CH-CH_2\cdot + Br \quad (20)$$

$$CH_2=CH-CH_2\cdot + CH_2=CH-CH_2Br \rightarrow CH_2=CH-CH_3 + CH_2=CH-\overset{\oplus}{C}HBr \quad (21)$$

$$Br + CH_2=CH-CH_2Br \rightarrow HBr + CH_2=CH-\overset{\oplus}{C}HBr \quad (22)$$

$$2CH_2=CH-\overset{\oplus}{C}HBr \rightarrow C_6H_6 + 2HBr \quad (23)$$

$$2CH_2=CH-CH_2\cdot \rightarrow CH_2=C=CH_2 + CH_2=CH-CH_3. \quad (24)$$

Ethene and methane are probably results of a side reaction involving the decomposition of propene and subsequent hydrogen abstraction.

Experimental Results: Allyl Fluoride (3-fluoropropene)

Figure 8:
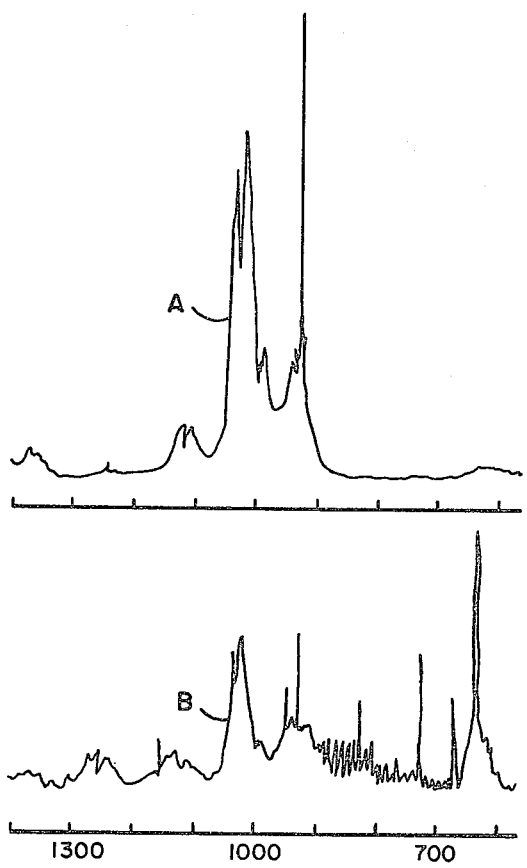
FIG. 8 depicts an infrared spectra of allyl fluoride and the products produced from laser induced chemical reactions.

Allyl fluoride exhibits infrared absorptions between 1050 and 900 cm$^{-1}$, and the most intense maxima are near 1020 and 930 cm$^{-1}$ (see FIG. 8 curve A). The P(32), 931.00 cm$^{-1}$ and the P(32) [00°1–02°0; 1035.41 cm$^{-1}$] lines of the CO$_2$ laser are resonant with the bands of allyl fluoride. These lines are used as the excitation frequencies.

The spectrum curve B of FIG. 8 is representative of the mixture of products which form when allyl fluoride gas is exposed to the CO$_2$ laser. The principal products are propyne, allene, and hydrogen fluoride. Smaller relative amounts of acetylene and ethylene are formed, and trace amounts of benzene, propene, methyl fluoride, and vinyl fluoride are identified in the infrared spectrum (see Table I). There have been no pyrolysis studies of allyl fluoride reported in the literature. In contrast to the other allyl halides, allyl fluoride appears to decompose more by a unimolecular reaction as opposed to the radial non-chain reaction. This is not surprising in view of the fact that C—F bond dissociation energies are relatively large (larger than for other C-halogen bonds and some C—C bonds as well).

Instead of allene isomerizing to propyne, another possibility exists for allyl fluoride. The amount of cisisomer varies from 4% in allyl bromide to 45% in allyl fluoride.

In the cis conformer, an interaction between the fluorine and γ hydrogen atoms is possible:

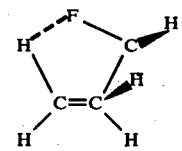

On excitation, this conformer could eliminate HF and form a biradical which could rearrange to propyne.

From the observed products, an overall mechanism for allyl fluoride is represented by $$CH_2=CH-CH_2F \longrightarrow C_2=C=CH_2 + HF \quad (25)$$

$$CH_2=CH-CH_2F \longrightarrow \dot{C}H=CH-\dot{C}H_2 + HF \quad (26)$$
$$\downarrow$$
$$HC\equiv C-CH_3 + HF$$

$$CH_2=CH-CH_2F \longrightarrow CH_2=CH\cdot + CH_2F\cdot \quad (27)$$

$$CH_2=CH\cdot \longrightarrow CH\equiv CH + H\cdot \quad (28)$$

$$CH_2=CH\cdot + CH_2=CH-CH_2F \longrightarrow \quad (29)$$
$$CH_2=CH_2 + CH_2=CH-CHF$$

$$\longrightarrow CH_2=CHF + CH_2-CH=CH_2 \quad (30)$$

$$CH_2F\cdot + CH_2=CH_2F \longrightarrow CH_3F + CH_2=CH-CHF \quad (31)$$

$$2CH_2=CH-CHF \longrightarrow C_6H_6 + 2HF. \quad (32)$$

The smaller yields of radical products are an indication that Reactions (25) and (26) are the preferred initial reaction paths.

The sample of allyl fluoride was insufficient to perform any kinetic experiments.

Experimental Results: 2,3-dichloropropene and 2-methyl-3-chloropropene

To determine if substituted benzenes can also be produced by laser-induced reactions, experiments with 2,3-dichloropropene and 2-methyl-3-chloropropene were performed. If these compounds follow similar mechanisms as allyl chloride, the mono- and di-substituted benzenes should be observed. When 2,3-dichloropropene was irradiated, HCl, propargyl chloride (H—C≡C—CH$_2$Cl), benzene, chlorobenzene, allene, ethylene, chloroallene and acetylene are the only products observed (see Table III).

Irradiation of 2-methyl-3-chloropropene produces HCl, propyne, benzene. toluene, allene, isobutene, ethene, acetylene and methane. Again the di-substituted benzene (xylene) is not observed.

These reactions show that substituted benzenes can be formed by laser irradiation.

Although some of the reaction products are the same for these two compounds as for allyl chloride, different radicals and reaction paths must be operative. A highly reactive carbon is also indicated by the formation of benzene and only the mono-substituted benzene.

As earlier referenced herein, Tables I, II, and III, depict, respectively, infrared bonds (cm$^{-1}$) of products of the laser-induced decomposition reaction of allyl halides, concentration of remaining allyl chloride after irradiation and calculated reaction order, and infrared bonds (cm$^{-1}$) of products of the laser-induced decomposition reactions of 2-methyl-3-chloropropene (MCP) and 2,3-dichloropropene (DCP).

TABLE I

Infrared Bands (cm$^{-1}$) of Products of the Laser-Induced Decomposition Reactions of Allyl Halides.[a]

| Allyl Fluoride | Allyl Chloride | Allyl Bromide | Identify |
|---|---|---|---|
| 633 | 633 | 633 (trace) | propyne ($C_3H_4$) |
|  | 658 |  | 1,3-cyclohexadiene ($C_6H_8$) |
|  | 664 |  | unidentified |
| 674 | 674 | 674 | benzene ($C_6H_6$) |
| 729 | 729 | 729 | acetylene ($C_2H_2$) |
| 800–900 | 800–900 | 800–900 (trace) | allene ($C_3H_4$)[b] |
| 830 |  |  | unidentified |
| 912 (trace) | 912 | 912 | propene ($C_3H_6$) |
| 929 |  |  | vinyl fluoride ($C_2H_3F$) |
| 949 | 949 | 949 | ethylene ($C_2H_4$) |
| 990 (trace) | 990 | 990 | propene |
|  | 1038 | 1038 | benzene |
| 1048 |  |  | methylfluoride ($CH_3F$) |
| 1156 |  |  | vinyl fluoride |
| 1249 |  |  | propyne |
| 1275 |  |  | unidentified |
| 1306 | 1306 |  | methane ($CH_4$) |
|  |  | 2400–2700 | hydrogen bromide (HBr)[c] |
|  | 2700–3000 |  | hydrogen chloride (HCl)[c] |
| 3334 |  |  | propyne |
| 3700–4000 |  |  | hydrogen fluoride (HF)[c] |

[a]Only the major bands for a given compound are listed.
[b]Allene exhibits a perpendicular band whose Q branches are 808, 818, 827, 836, 845, 854, 862, 869, and 876 cm$^{-1}$.
[c]The hydrogen halides exhibit parallel bands whose P and R branches cover these respective regions.

TABLE II

Concentration of Remaining Allyl Chloride After Irradiation and Calculated Reaction Order

| Irradiation Time | 40 Torr Allyl Chloride (Torr) | 80 Torr Allyl Chloride (Torr) | Reaction Order* |
|---|---|---|---|
| 0.1 | 39.3 |  |  |
| 0.2 | 38.7 | 74.5 | 2.08 |
| 0.4 | 35.5 | 67.2 | 1.51 |
| 0.7 | 32.8 | 56.3 | 1.72 |
| 1.0 | 29.5 | 48.5 | 1.58 |
| 1.3 | 27.4 | 42.0 | 1.59 |
| 1.6 | 24.4 | 37.5 | 1.45 |
| 1.9 | 22.5 | 33.5 | 1.41 |

*Reaction order = $\frac{\ln(\text{Rate 2/Rate 1})}{\ln(2)}$

TABLE III

Infrared Bands (cm$^{-1}$) of Products of the Laser-induced Decomposition Reactions of 2-Methyl-3 Chloropropene (MCP) and 2,3-Dichloropropene (DCP)

| MCP | DCP | Identity |
|---|---|---|
| 633 |  | propyne |
|  | 638 |  |
|  | 646 | propargyl chloride |
|  | 654 |  |
| 674 | 674 | benzene |
|  | 685 | chlorobenzene |
| 694 |  | toluene |
| 730 | 730 | acetylene & toluene |
|  | 742 | chlorobenzene |
|  | 760 P |  |
|  | 768 Q | chloroallene |
|  | 774 R |  |
| 900–800 | 900–800 | allene[a] |
| 889 |  | isobutylene |
| 950 | 950 | $C_2H_2$ |
|  | 960 | chloroallene |
|  | 1095 | chloroallene |
| 1307 |  | $CH_4$ |

[a]see Table I.

CONCLUSIONS

The allyl halides constitute a very interesting family of compounds. The results obtained from the laser-induced reactions show that the fluoride, chloride and bromide all decompose by slightly different mechanisms. This can be directly related to the strength of the C—X bond and the halide reactivity.

In allyl bromide, breaking the C—Br bond is the lowest energy path for decomposition. Unimolecular and other bond-breaking reactions appear to be sufficiently different in energy to occur. As in pyrolysis, LIR proceeds by a radical non-chain mechanism.

The C—Cl bond is also the weakest in allyl chloride. Pyrolysis can best be explained as the initial breaking of this bond. It is also observed in pyrolysis at $\geq 1000°$ C. larger quantities of $C_2$ compounds are produced. Diallyl decomposition was suggested as the main source of these $C_2$ and $C_4$ compounds although the yield of $C_4$ compounds did not increase in proportion to the $C_2$ compounds. The amount of $C_2$ compounds was even greater in the present experiments. Other explanations for the greater amounts of $C_2$ compounds exist. Raising the temperature could cause decomposition of products such as propene or allow alternate reaction paths such as breaking the C—C bond in allyl chloride to occur. The latter is believed to occur in the LIR experiments and to some degree in pyrolysis.

Although initially the photon concentration is too low for mode-selective decomposition, over the length of irradiation time a sufficient number of photons are present for multiphoton absorption and decomposition. Since the $CO_2$ laser absorption is in the $CH_2$ wag and C—C stretching modes, all of the absorbed energy must be redistributed to the C—Cl bond for its dissociation. The C—C and C—Cl bond energies are not widely separated in energy and some of the higher energy paths would be expected at higher temperatures. This is apparently observed in pyrolysis. If a weak coupling exists between the C—C stretch and the C—Cl stretch, a non-randomization of energy could occur, leading to a non-statistical dissociation along the higher energy path. This is believed to occur for the laser-induced reaction.

The observation of many products points out the complexity of the allyl chloride reaction mechanism compared to allyl bromide. The observed induction period and deviation from first-order kinetics are indicative of a radical chain mechanism.

As in pyrolysis some radical non-chain reactions are also present.

In allyl fluoride the C—F bond is approximately of equal bond strength with the C—C bond and the C—H carbon bond. Unlike the other halides, fluorine atoms are much more reactive and would not be expected on decomposition of fluoro-compounds. The presence of large quantities of allene and propyne indicates, as expected, a different initial reaction in allyl fluoride. The decomposition follows primarily a unimolecular reaction with the loss of HF. Some C—C bond dissociation is also indicated from the observed products. Therefore a radical chain mechanism is also partially operative.

We claim:

1. A method for laser photochemical synthesis of benzene and substituted benzene comprising:
   i. filling one or more laser reaction cells with an allyl halide selected from allyl chloride, 2-methyl-3-chloropropene, 2,3-dichloropropene, allyl bromide, and allyl fluoride to a pressure from about 10 to about 100 torr;
   ii. irradiating said selected allyl halide with a power level from about 25 to about 150 watts of a cw $CO_2$ tunable laser, tuned to a radiation line selected that is resonant with an absorption band of said allyl halide, said irradiating accomplished over a time period from about 0.2 second to about 60 seconds by employing said cw $CO_2$ tunable laser tuned to radiation line such as P(36), 929.02 $cm^{-1}$, P(32), 931.00 $cm^{-1}$, P(26), [00°1–10°0] 938.69 $cm^{-1}$, or P(22), 942.38 $cm^{-1}$ with the specified frequencies being resonant with said absorption band of said allyl halide selected to thereby achieve dissociation of said allyl halide and to achieve a laser-induced photochemical synthesis of benzene and substituted benzene.

2. The method of claim 1 wherein said allyl halide selected is allyl chloride, said pressure is from about 50 to 100 torr, and said irradiating is accomplished with the P(26) [00°1–10°0]line of said cw $CO_2$ laser at 938.69 $cm^{-1}$ to produce benzene having an infrared major band of 674 $cm^{-1}$ and 1038 $cm^{-1}$.

3. The method of claim 1 wherein said allyl halide selected is allyl bromide, said pressure is about 25 torr, and said irradiating is accomplished with the P(36) line of said cw $CO_2$ laser at 929.02 $cm^{-1}$ to produce benzene having infrared major bands at 674 $cm^{-1}$ and 1038 $cm^{-1}$.

4. The method of claim 1 wherein said allyl halide selected is allyl bromide, said predetermined pressure is about 50 torr, and said irradiating is accomplished with the P(22) line of said cw $CO_2$ laser at 942.02 $cm^{-1}$ to produce benzene having infrared major bands at 674 $cm^{-1}$ and 1038 $cm^{-1}$.

5. The method of claim 1 wherein said allyl halide selected is allyl fluoride, said irradiating is accomplished with a time of about 10 seconds at a power level of about 100 watts with the P(32) line of said cw $CO_2$ tunable laser to produce benzene having an infrared major band at 674 $cm^{-1}$.

6. The method of claim 1 wherein said allyl halide selected is 2,3-dichloropropene and wherein said irradiating produce benzene having an infrared major band at 674 $cm^{-1}$ and the substituted benzene chlorobenzene having an infrared major band at 742 $cm^{-1}$.

7. The method of claim 1 wherein said allyl halide selected is 2-methyl-3-chloropropene and wherein said irradiating produce benzene having an infrared major band at 674 $cm^{-1}$ and the substituted benzene (toluene) having an infrared major band at 694 $cm^{-1}$.

* * * * *